(12) United States Patent
Law et al.

(10) Patent No.: US 7,202,004 B2
(45) Date of Patent: *Apr. 10, 2007

(54) ELECTROPHOTOGRAPHIC ORGANOPHOTORECEPTORS WITH NOVEL CHARGE TRANSPORT MATERIALS

(75) Inventors: Kam W. Law, Woodbury, MN (US); Nusrallah Jubran, St. Paul, MN (US); Zbigniew Tokarski, Woodbury, MN (US)

(73) Assignee: Samsung Electronics Co., Ltd., Su-won (KR)

( * ) Notice: Subject to any disclaimer, the term of this patent is extended or adjusted under 35 U.S.C. 154(b) by 0 days.

This patent is subject to a terminal disclaimer.

(21) Appl. No.: 10/982,320

(22) Filed: Nov. 4, 2004

(65) Prior Publication Data

US 2005/0058917 A1 Mar. 17, 2005

Related U.S. Application Data

(62) Division of application No. 10/256,629, filed on Sep. 27, 2002, now Pat. No. 7,118,839.

(60) Provisional application No. 60/347,051, filed on Jan. 8, 2002, provisional application No. 60/330,377, filed on Oct. 18, 2001, provisional application No. 60/329,275, filed on Oct. 12, 2001, provisional application No. 60/329,121, filed on Oct. 12, 2001, provisional application No. 60/325,735, filed on Sep. 28, 2001, provisional application No. 60/325,734, filed on Sep. 28, 2001, provisional application No. 60/325,717, filed on Sep. 28, 2001, provisional application No. 60/325,714, filed on Sep. 28, 2001.

(51) Int. Cl.
G03G 13/10 (2006.01)
G03G 5/047 (2006.01)
(52) U.S. Cl. ............... 430/117; 430/58.45; 430/79
(58) Field of Classification Search ............. 430/58.15, 430/58.2, 58.4, 58.45, 58.55, 58.5, 58.6, 430/79, 78, 72, 75, 76, 117
See application file for complete search history.

(56) References Cited

U.S. PATENT DOCUMENTS 4,297,426 A 10/1981 Sakai et al.
(Continued)

FOREIGN PATENT DOCUMENTS

GB 1047525 9/1966
(Continued)

OTHER PUBLICATIONS

Grant, R.et al., ed., *Grant & Hackh's Chemical Dictionary*, fifth edition, McGraw-Hill Book Co., NY (1987), p. 80.*

(Continued)

Primary Examiner—Janis L. Dote
(74) Attorney, Agent, or Firm—Patterson, Thuente, Skaar & Christensen, P.A.

(57) ABSTRACT

An organophotoreceptor that includes:
(a) a charge transport compound having the formula

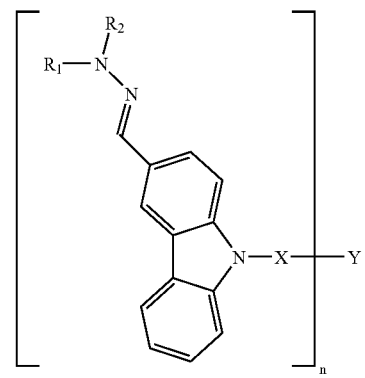

where n is an integer between 2 and 6, inclusive;
$R_1$ is an aryl group;
$R_2$ is a sulfolanyl group; a pyrrolyl group; a tetrazolyl group; a benzotriazolyl group; a stilbenyl group; an alkylsulfonylphenyl group, an arylsulfonylphenyl; a pyrazolyl group; or group A, wherein A is represented by the formula

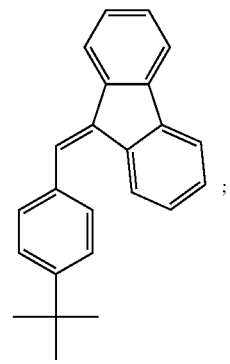

with the proviso that when $R_2$ is an alkylsulfonylphenyl group or an arylsulfonylphenyl, $R_1$, may be hydrogen, an alkyl group, or an aryl group;
X is an alkylene linking group having the formula $-(CH_2)_m-$, where m is an integer between 0 and 20, inclusive; and
Y is a bond, C, N, O, S, a $-(CH_2)_p-$ group where p is an integer between 0 and 10, an aryl group, a cycloalkyl group, a cyclosiloxyl, a heterocyclic group, or a $CR_7$ group where $R_7$ is H, an alkyl group, or aryl group;
(b) a charge generating compound; and
(c) an electrically conductive substrate.

13 Claims, No Drawings

U.S. PATENT DOCUMENTS

| | | | |
|---|---|---|---|
| 4,476,137 A | 10/1984 | Haviv et al. | |
| 4,786,571 A | 11/1988 | Ueda | |
| 4,957,838 A | 9/1990 | Aruga et al. | |
| 5,128,227 A | 7/1992 | Monbaliu et al. | |
| 5,274,116 A | 12/1993 | Martin et al. | |
| 5,932,384 A | 8/1999 | Mitsumori et al. | |
| 6,001,522 A | 12/1999 | Woo et al. | |
| 6,020,096 A | 2/2000 | Fuller et al. | |
| 6,030,734 A | 2/2000 | Mitsumori | |
| 6,066,426 A | 5/2000 | Mott et al. | |
| 6,099,996 A | 8/2000 | Yanus et al. | |
| 6,140,004 A | 10/2000 | Mott et al. | |
| 6,214,503 B1 | 4/2001 | Gaidelis et al. | |
| 6,340,548 B1 | 1/2002 | Jubran et al. | |
| 6,864,025 B2 * | 3/2005 | Law et al. | 430/58.6 |

FOREIGN PATENT DOCUMENTS

| | | | |
|---|---|---|---|
| JP | 60-237453 | * | 11/1985 |
| JP | 62-116943 | * | 5/1987 |
| JP | 63-013048 | * | 1/1988 |
| JP | 05-148210 | | 6/1993 |
| WO | WO00/22483 | | 4/2000 |
| WO | WO01/71430 | | 9/2001 |

OTHER PUBLICATIONS

Atherton et al. "Synthesis of 3(s)-Acylamino-1[(Phenyl)(1H-Tetrazol-5-YL) Amino]-2-Azetidinones," Tetrahedron, 39(15)2599-2608 (1983).

Boyd et al., "The Dimerisation of 5-Methylene-Δ2-1-3-4-oxadiaolines" J. Chem. Soc.(C), 12: 2314-17, (1971).

Murakami et al., "An Efficient Synthesis of 1, 1Disubstituted Hydraines," Chem. & Pharmaceutical Bulletin 31(2):423-428, (1983).

* cited by examiner

ELECTROPHOTOGRAPHIC ORGANOPHOTORECEPTORS WITH NOVEL CHARGE TRANSPORT MATERIALS

CROSS REFERENCE TO RELATED APPLICATIONS

This application is a divisional application of U.S. patent application Ser. No. 10/256,629, filed on Sep. 27, 2002, now U.S. Pat. No. 7,118,839, which claims priority to U.S. Provisional Patent Application Ser. Nos. 60/325,714, filed Sep. 28, 2001; 60/325,735, filed Sep. 28, 2001; 60/325,717, filed Sep. 28, 2001; 60/325,734, filed Sep. 28, 2001; 60/329,275, filed Oct. 12, 2001; 60/329,121, filed Oct. 12, 2001; 60/330,377, filed Oct. 18, 2001, and 60/347,051, filed Jan. 8, 2002.

BACKGROUND OF THE INVENTION

1. Field of the Invention

This invention relates to organophotoreceptors suitable for use in electrophotography and, more specifically, to flexible organophotoreceptors having novel charge transport compounds comprising at least two carbazolecarboxaldehyde substituted-hydrazone groups.

2. Background of the Art

In electrophotography, an organophotoreceptor in the form of a plate, a flexible belt, a disk, a rigid drum, or a sheet around a rigid or compliant drum having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas (referred to as latent image). A liquid or solid toner is then provided in the vicinity of the latent image, and the toner particles deposit in either the charged or uncharged areas to create a toned image on the surface of the photoconductive layer. The resulting visible toner image can be transferred to a suitable receiving surface such as paper, or the photoconductive layer can operate as a permanent receptor for the image. The imaging process can be repeated many times.

Both single layer and multilayer photoconductive elements have been used. In the single layer embodiment, a charge transport material and charge generating material are combined with a polymeric binder and then deposited on an electrically conductive substrate. In the multilayer embodiment, the charge transport material and charge generating material are in the form of separate layers, each of which can optionally be combined with a polymeric binder and deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes or electrons) upon exposure to light. The purpose of the charge transport material is to accept these charge carriers and transport them through the charge transport layer in order to discharge a surface charge on the photoconductive element. When a charge transport compound is used, the charge transport compound accepts the hole carriers and transports them through the layer in which the charge transport compound is located. When an electron transport compound is used, the electron transport compound accepts the electron carriers and transports them through the layer in which the electron transport compound is located.

To produce high quality images, particularly after multiple cycles, it is desirable for the charge transport material to form a homogeneous solution with the polymeric binder and remain in solution. In addition, it is desirable to maximize the amount of charge which the charge transport material can accept (indicated by a parameter known as the acceptance voltage or "$V_{acc}$"), and to minimize retention of that charge upon discharge (indicated by a parameter known as the residual voltage or "$V_{res}$").

There are many charge transport materials available for electrophotography. The most common charge transport materials are pyrazoline derivatives, fluorene derivatives, oxadiazole derivatives, stilbene derivatives, hydrazone derivatives, carbazole hydrazone derivatives, triphenylamine derivatives, julolidine hydrazone derivatives, polyvinyl carbazole, polyvinyl pyrene, or polyacenaphthylene. However, each of the above charge transport materials suffer some disadvantages. There is always a need for novel charge transport materials to meet the various requirements of electrophotography applications.

SUMMARY OF THE INVENTION

In a first aspect, the invention features an organophotoreceptor that includes:

(a) a charge transport compound having the formula

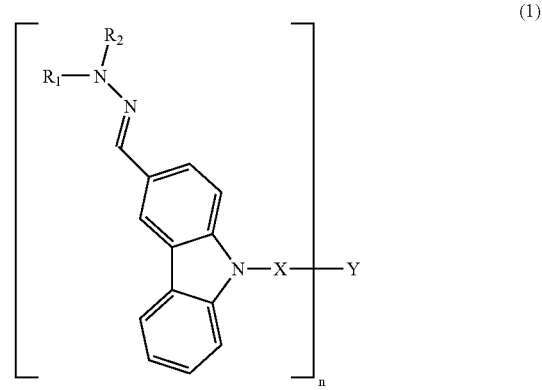

where n is an integer between 2 and 6, inclusive;

$R_1$ is an aryl group (e.g., a phenyl, naphthyl group, stilbenyl, benzyl, or tolanyl group);

$R_2$ is selected from the group consisting of a sulfolanyl group, a pyrrolyl group; a tetrazolyl group; a benzotriazolyl group; a stilbenyl group; an alkylsulfonyiphenyl group, an arylsulfonylphenyl; a pyrazolyl group; and group A, wherein A is represented by the formula

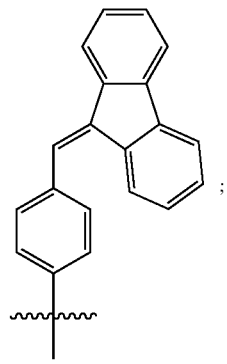

with the provision that when $R_2$ is an alkylsulfonylphenyl group or an arylsulfonylphenyl, $R_1$ may be hydrogen, an alkyl group, or an aryl group, X is a linking group having the formula —$(CH_2)_m$—, where m is an integer between 0 and 20, inclusive, and one or more of the methylene groups is optionally replaced by an oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or aryl group; and Y is a bond, carbon atom, nitrogen atom, oxygen atom, sulfur atom, a —$(CH_2)_p$— alkylene group where p is an integer between 0 and 10 (in the alkylene group, hydrogen atoms on the group may be removed to provide bond positions to enable n to have a higher value than 2), an aliphatic group, an aryl group, a cycloallcyl group, a cyclosiloxyl group (e.g., a cyclotetrasiloxyl group), a heterocyclic group, or a $CR_7$ group where $R_7$ is hydrogen atom, an alkyl group, or aryl group;

(b) a charge generating compound; and (c) an electrically conductive substrate.

It is understood in this definition that in such situations where Y is limited by its definition to a selection that has a specific number or limit of bonds (e.g., a bond may allow n to be only 2, an oxygen atom will allow n to be only 2, a carbon atom will allow n to be a maximum of 4 in a tetra-substituted modality, N will allow n to be a maximum of 3 (although a quaternary ammonium salt is a possibility, without altering the generic structure (1) of the compound), and the like. The reading of this description is readily understood by those of ordinary skill in the art and is not contrary to common usage of the terms or antagonistic to chemical notation. The alternatives are read by those skilled in the art to exclude those combinations that are understood to be impossible as a convenience of drafting.

The charge transport compound may or may not be symmetrical. Thus, for example, a linking group X for any given "arm" of the compound may be the same or different from the linking groups in other "arms" of the compound. Similarly, $R_1$ and $R_2$ groups for any given "arm" of the compound may be the same or different from $R_1$ and $R_2$ groups in any other arm. In addition, the above-described formula for the charge transport compound is intended to cover isomers.

The organophotoreceptor may be provided in the form of a plate, a flexible belt, a disk, a rigid drum, or a sheet around a rigid or compliant drum. In one embodiment, the organophotoreceptor includes: (a) a charge transport layer comprising the charge transport compound and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate.

In a second aspect, the invention features an electrophotographic imaging apparatus that includes (a) a plurality of support rollers; and (b) the above-described organophotoreceptor in the form of a flexible belt threaded around the support rollers. The apparatus preferably further includes a liquid toner dispenser.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a liquid toner that includes a dispersion of colorant particles in an organic liquid to create a toned image; and (d) transferring the toned image to a substrate.

In a fourth aspect, the invention features a novel charge transport material having the formula

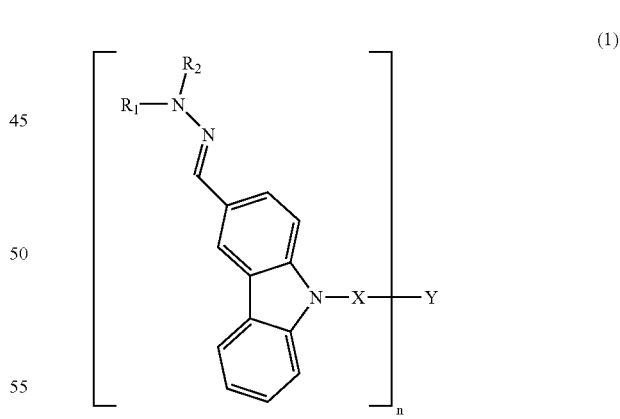

(1)

where n is an integer between 2 and 6, inclusive;

$R_1$ is an aryl group (e.g., a phenyl group, naphthyl group, stilbenyl group, benzyl group, or tolanyl group);

$R_2$ is a sulfolanyl group, a pyrrolyl group; a tetrazolyl group; a benzotriazolyl group; a stilbenyl group; an alkylsulfonylphenyl group, an arylsulfonylphenyl; a pyrazolyl group; and a group A, wherein A is represented by the formula

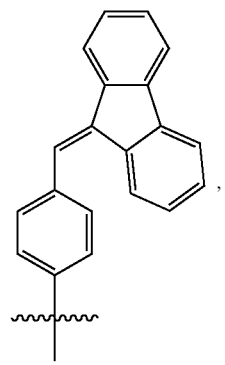

with the provision that when $R_2$ is an alkylsulfonylphenyl group or an arylsulfonylphenyl, $R_1$ may be hydrogen, an alkyl group, or an aryl group;

X is a linking group having the formula —$(CH_2)_m$—, where m is an integer between 0 and 20, inclusive, and one or more of the methylene groups is optionally replaced by an oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or aryl group; and Y is a bond, carbon atom, nitrogen atom, oxygen atom, sulfur atom, a alkylene (—$(CH_2)_p$—) group where p is an integer between 0 and 10 (and where hydrogen atoms on the alkylene group may be removed to provide bond positions to enable n to have a higher value than 2), an aliphatic group, an aryl group, a cycloalkyl group, a cyclosiloxyl group (e.g., a cyclotetrasiloxyl group), a heterocyclic group, or a $CR_7$ group where $R_7$ is hydrogen atom, an alkyl group, or aryl group.

In one embodiment, a charge transport compound is selected in which $R_1$ is phenyl, $R_2$ is a sulfolanyl group, n is 2, X is —$(CH_2)_m$— group where m is an integer between 0 and 20, and Y is a bond or methylene group.

The charge transport compound may have the general formula:

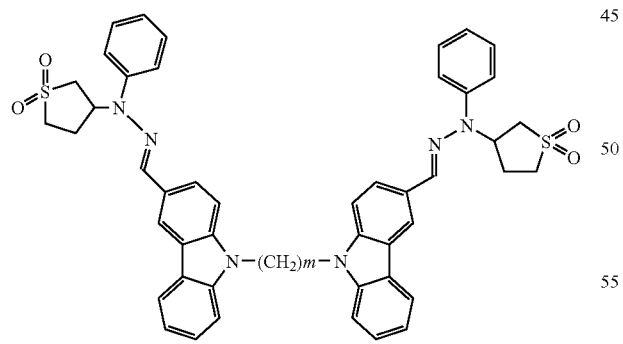

where m is an integer between 2 and 20.

When the term "group" or "nucleus" is used in this invention to describe a chemical compound or substituent, the described chemical material includes the basic group or nucleus and that group or nucleus with conventional substitution. Where the term "moiety" is used to describe a chemical compound or substituent, only the unsubstituted chemical material is intended to be included. For example, "alkyl group" includes not only such alkyl moieties as methyl, ethyl, octyl, stearyl, etc., but also such moieties bearing substituents groups such as halogen, cyano, hydroxyl, nitro, amine, carboxylate, etc. On the other hand, "alkyl moiety" or "alkyl" includes only methyl, ethyl, octyl, stearyl, cyclohexyl, etc.

These photoreceptors can be used successfully with liquid toners to produce high quality images. The high quality of the images is maintained after repeated cycling.

Other features and advantages of the invention will be apparent from the following description of the preferred embodiments thereof, and from the claims.

DETAILED DESCRIPTION OF THE INVENTION

The invention features organophotoreceptors that include charge transport compounds having the formulae:

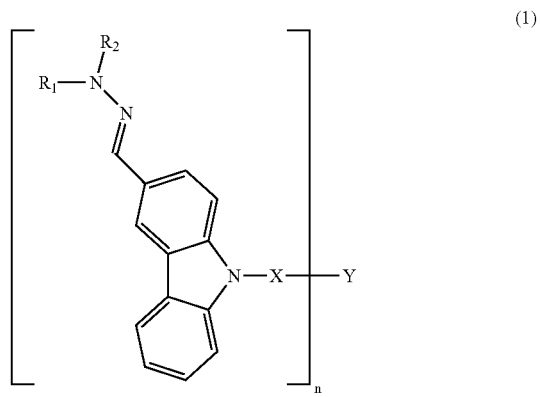

(1)

where a is an integer between 2 and 6, inclusive;

$R_1$ is an aryl group (e.g., a phenyl group, naphthyl group, stilbenyl group, benzyl group, or tolanyl group);

$R_2$ is a sulfolanyl group, a pyrrolyl group; a tetrazolyl group; a beuzotriazolyl group; a stilbenyl group; an alkylsulfonylphenyl group, an arylsulfonylphenyl; a pyrazolyl group; and group A, wherein A is represented by the formula

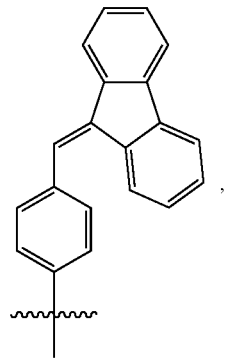

with the proviso that when $R_2$ is an alkylsulfonylphenyl group or an arylsulfonylphenyl, $R_1$ may be hydrogen, an alkyl group, or an aryl group;

X is a linking group selected from alkylene groups having the formula —$(CH_2)_m$—, where m is an integer between 0 and 20, inclusive, and one or more of the methylene groups in the alkylene group is optionally replaced by an oxygen atom, a carbonyl group, urethane, urea, an ester group, a —$NH_3$ group, a $CHR_4$ group, or a $CR_5R_6$ group where $R_3$, $R_4$, $R_5$, and $R_6$ are, independently, H, an alkyl group, or aryl group (in the optional use of replacement groups for the methylene groups, it should be appreciated that the replacement is for a portion of the methylene groups, not a replacement to remove all methylene groups, which would prevent the group from being a methylene group. A single methylene group may be substituted but not replaced. It is preferred that any substitution occur at a level where there are at least two methylene groups remaining in the linking group for each substituting group, preferably at least three methylene groups, and more preferably at least 4, 5 or 6 methylene groups remaining in the linking group for each substituted group); and Y is a bond, carbon atom, nitrogen atom, oxygen atom, sulfur atom, a ailcylene (—$(CH_2)_p$—) group where p is an integer between 0 and 10 (and where hydrogen atoms on the alkylene group may be removed to provide bond positions to enable n to have a higher value than 2), an aliphatic group, an aryl group, a cycloalkyl group, a cyclosiloxyl group (e.g., a cyclotetrasiloxyl group), a heterocyclic group, or a $CR_7$ group where $R_7$ is hydrogen atom, an alkyl group, or aryl group.

In one embodiment, a charge transport compound is selected in which $R_1$ is phenyl, $R_2$ is a sulfolanyl group, n is 2, X is an alkylene (—$(CH_2)_m$—) group where m is an integer between 0 and 20, and Y is a bond or methylene group.

Non-limiting examples of such charge transport compound have the following structures.

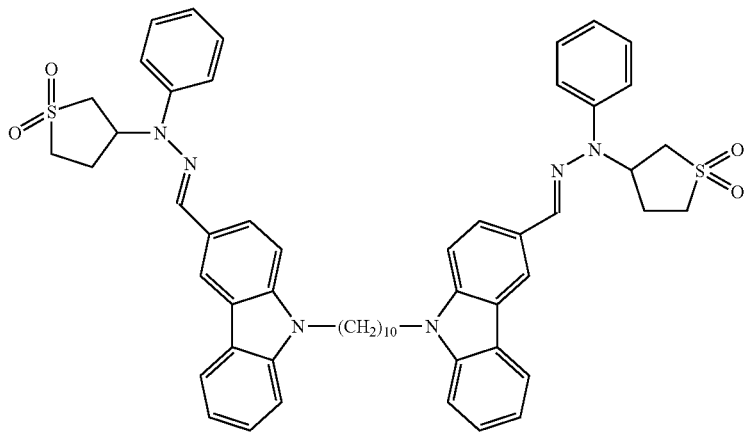

(2)

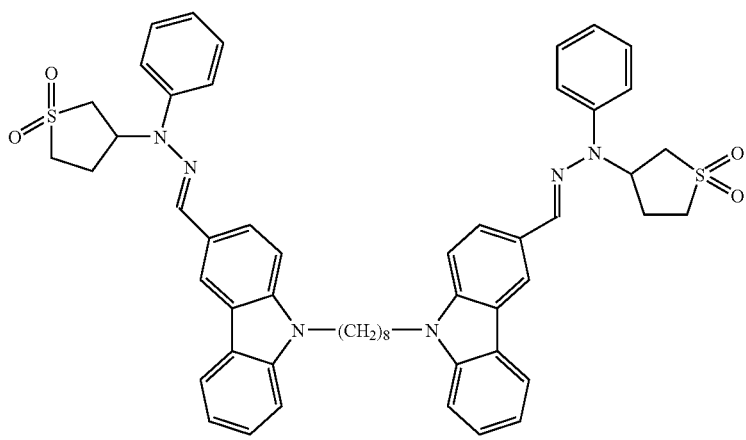

(3)

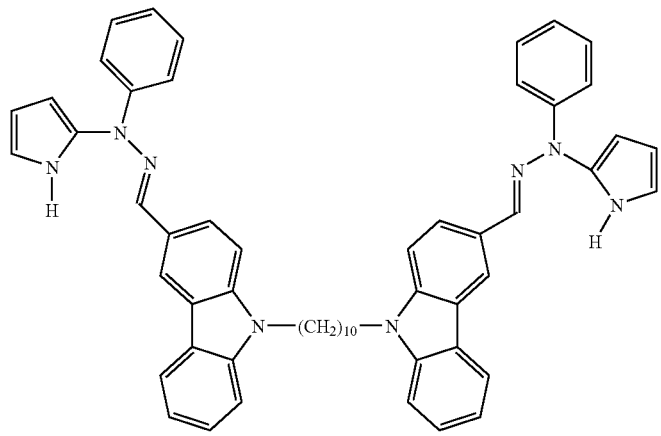
(4)
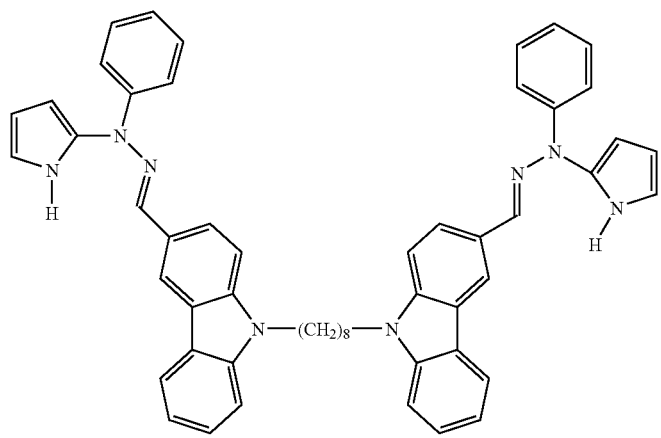
(5)
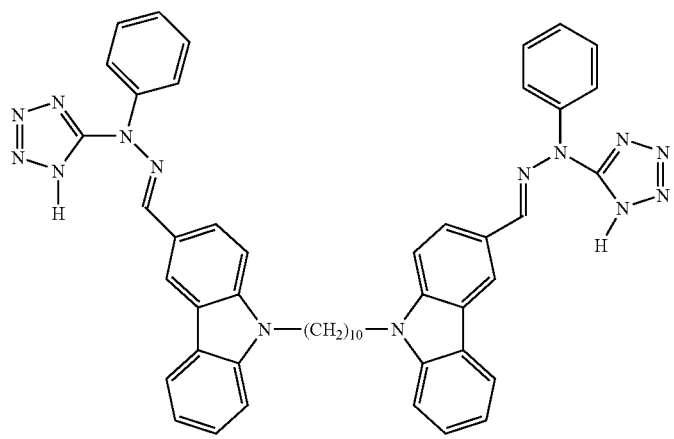
(6)

-continued
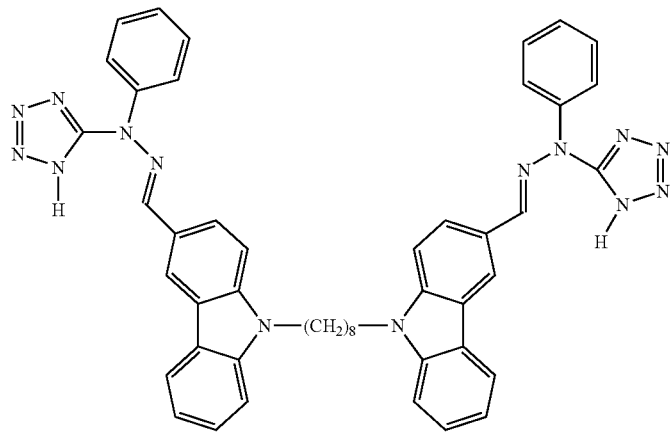
(7)
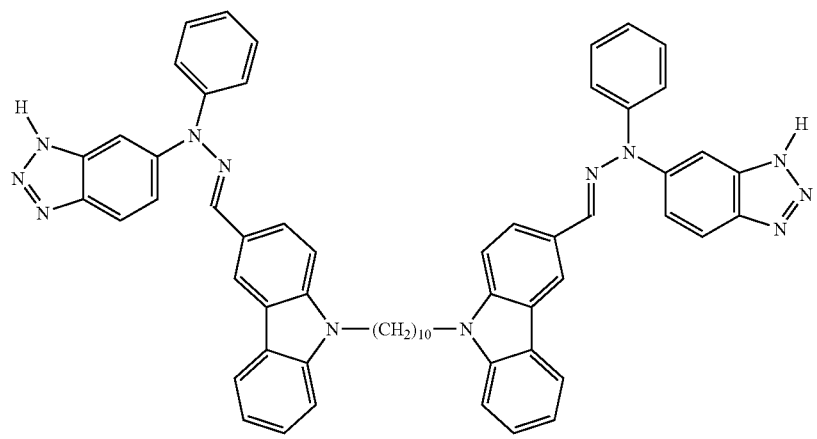
(8)
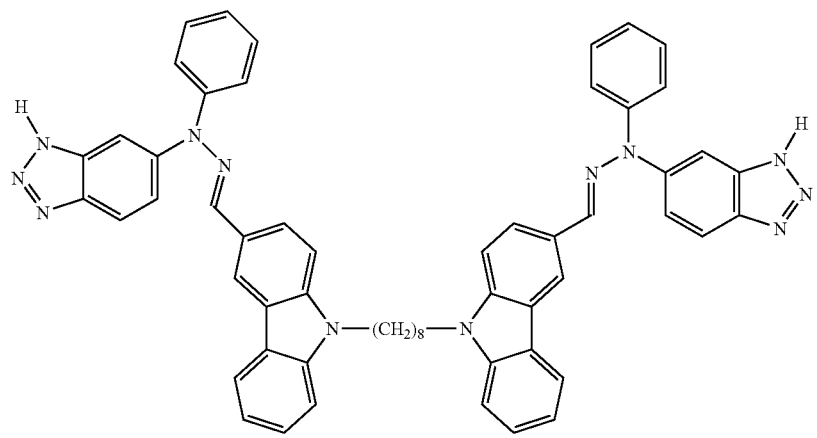
(9)

-continued
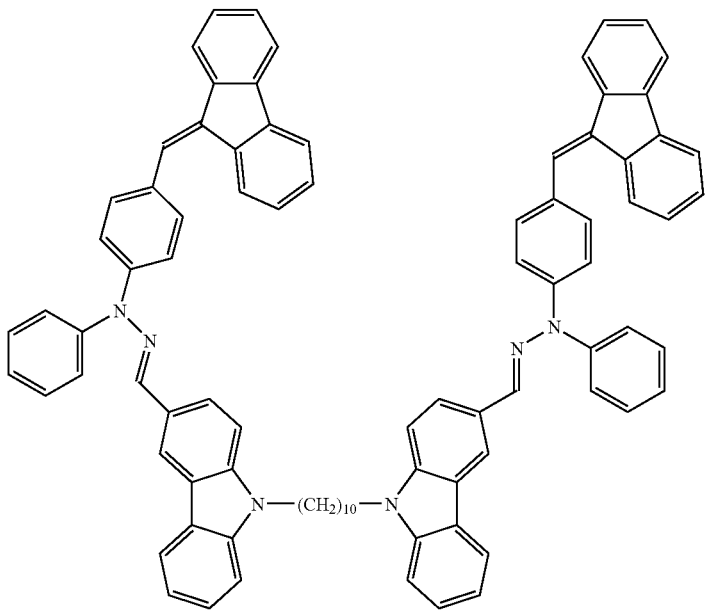
(10)
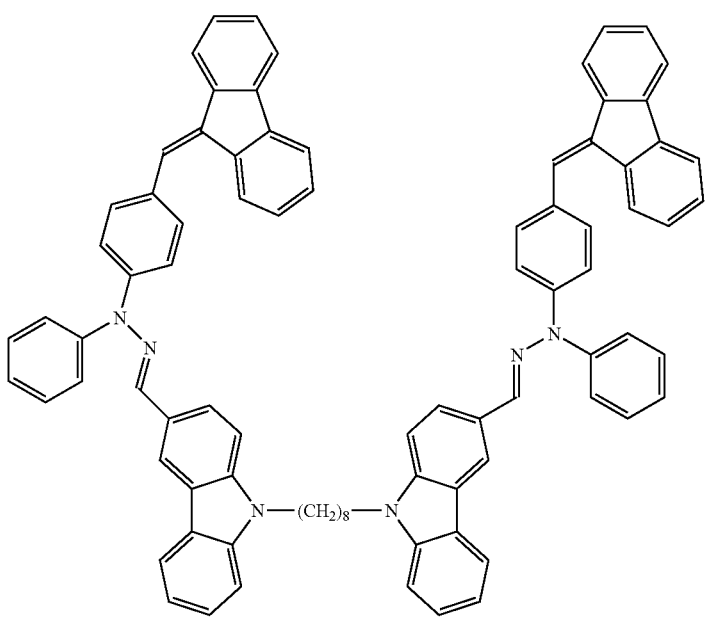
(11)

-continued
(12)
(13)
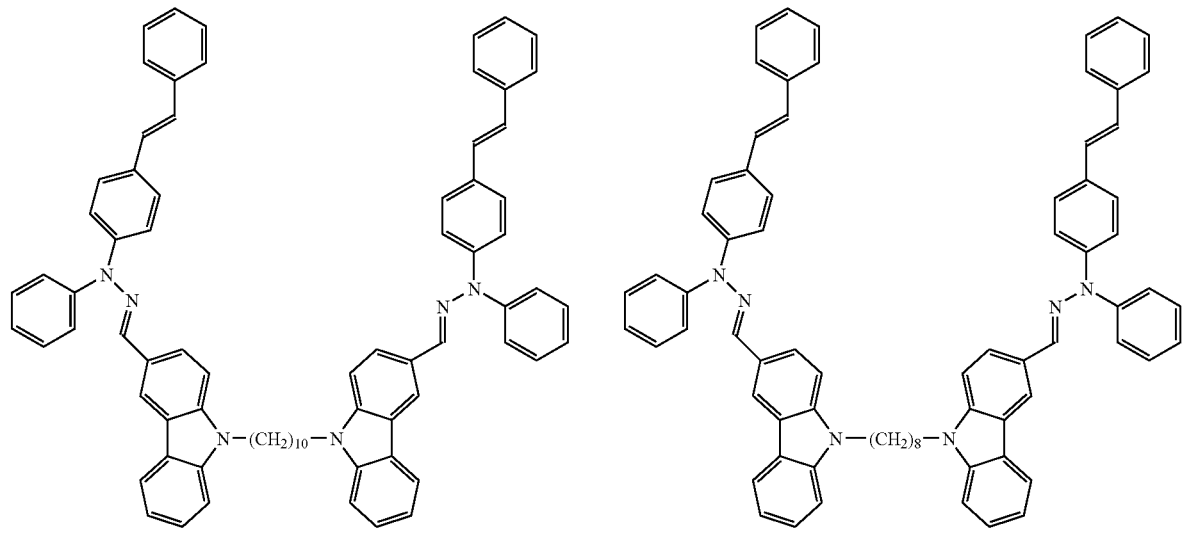
(14)
(15)
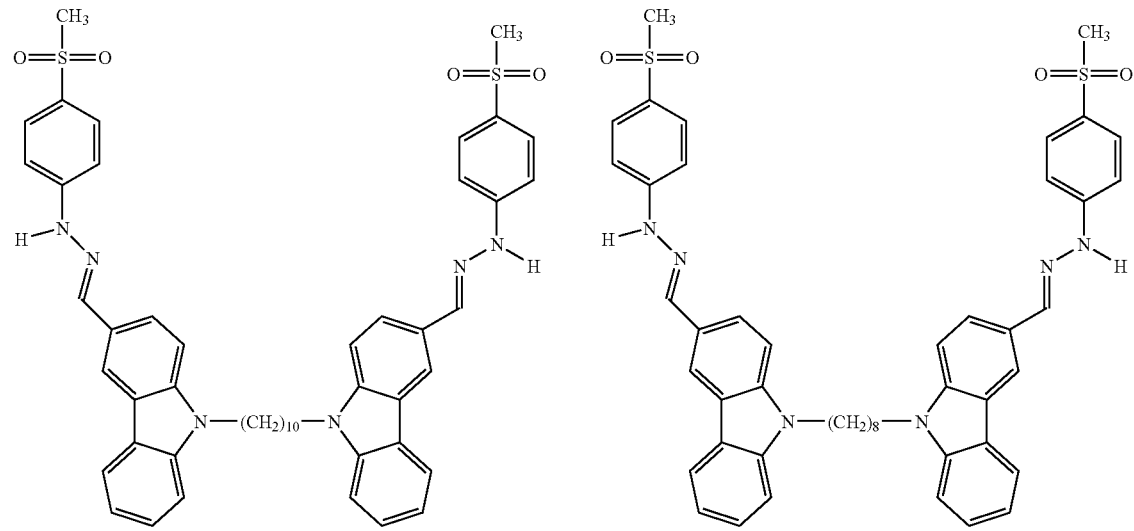
(16)
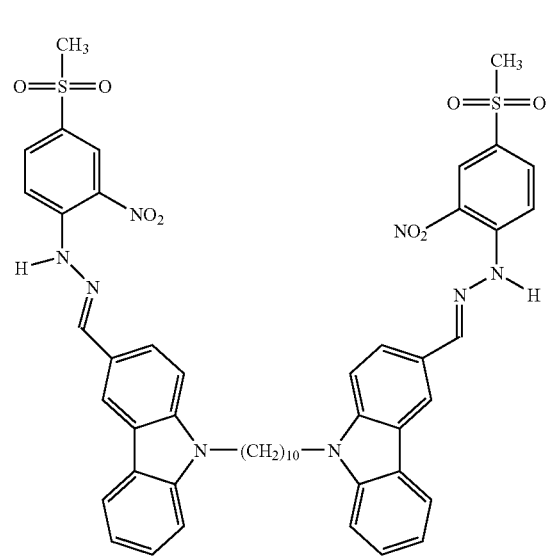

(17)

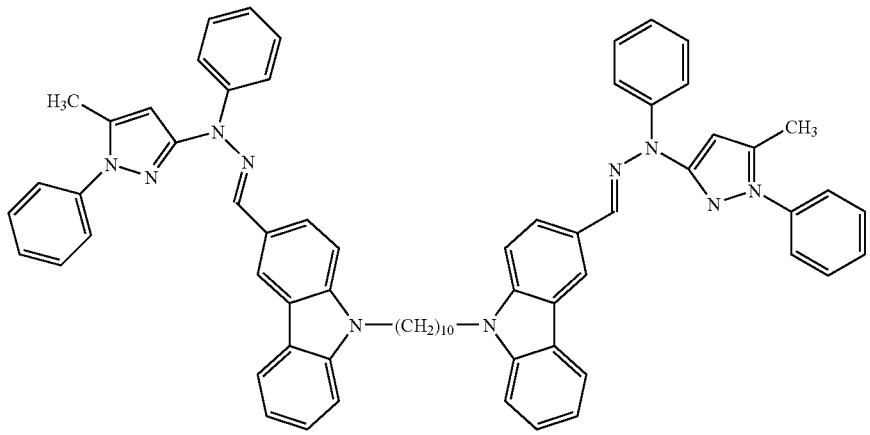

(18)

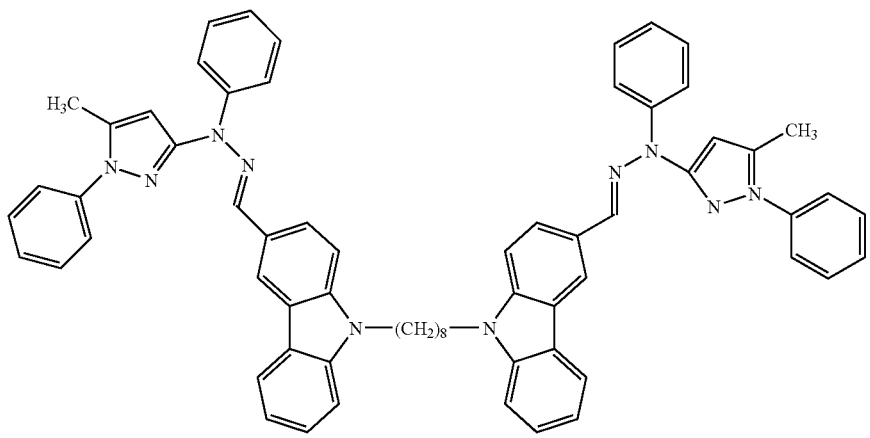

The organophotoreceptor may be in the form of a plate, a flexible belt, a disk, a rigid drum, or a sheet around a rigid or compliant drum, with flexible belts and rigid drums being preferred. The organophotoreceptor may include an electrically conductive substrate and a photoconductive element in the form of a single layer that includes both the charge transport compound and charge generating compound in a polymeric binder. Preferably, however, the organophotoreceptor includes an electrically conductive substrate and a photoconductive element that is a bilayer construction featuring a charge generating layer and a separate charge transport layer. The charge generating layer may be located intermediate between the electrically conductive substrate and the charge transport layer. Alternatively, the photoconductive element may be an inverted construction in which the charge transport layer is intermediate between the electrically conductive substrate and the charge generating layer.

The electrically conductive substrate may be flexible, for example in the form of a flexible web or a belt, or inflexible, for example in the form of a drum. Typically, a flexible electrically conductive substrate comprises of an insulated substrate and a thin layer of electrically conductive materials. The insulated substrate may be paper or a film forming polymer such as polyethylene terepthalate, polyimide, polysulfone, polyethylene naphthalate, polypropylene, nylon, polyester, polycarbonate, polyvinyl fluoride, polystyrene and the like. Specific examples of supporting substrates included polyethersulfone (STABAR™ S-100, available from ICI), polyvinyl fluoride (TEDLAR™, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodide, conductive polymers such as polypyroles and CALGON™ Conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. Preferably, the electrically conductive material is aluminum. Typically, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm.

The charge generating compound is a material which is capable of absorbing light to generate charge carriers, such as a dyestuff or pigment. Examples of suitable charge generating compounds include metal-free phthalocyanines (e.g., CGM-X01 x-form metal-free phthalocyanine from Sanyo Color Works, Ltd.), metal phthalocyanines such as titanium phthalocyanine, copper phthalocyanine, oxytitanium phthalocyanine, hydroxygallium phthalocyanine, squarylium dyes and pigments, hydroxy-substituted squarylium pigments, perylimides, polynuclear quinones available from Allied Chemical Corporation under the tradename INDOFAST™ Double Scarlet, INDOFAST™ Violet Lake B, INDOFAST™ Brilliant Scarlet and INDOFAST™ Orange, quinacridones available from DuPont under the tradename MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulfoselenide, cadmiumselenide, cadmium sulfide, and mixtures thereof. Preferably, the charge generating compound is oxytitanium phthalocyanine, hydroxygallium phthalocyanine or a combination thereof.

The binder is capable of dispersing or dissolving the charge transport material of this invention and the charge generating compound. Examples of suitable binders include polystyrene-co-butadiene, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, resol, poly(phenylglycidyl ether)-co-dicyclopentadiene, copolymers of monomers used in the above-mentioned polymers, and combinations thereof. Polycarbonate binders are particularly preferred. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates.

If a particular charge transport material of this invention works as a charge transport compound, optionally, the organophotoreceptor of this invention may contain an electron transport compound. Non-limiting examples of suitable electron transport compound include bromoanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitroindeno4H-indeno[1,2-b]thiophene-4-one, and 1,3,7-trinitrodibenzothiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1, 1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethyl-idene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11, 12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxycarbonyl)methylene]anthrone, 1,8-dihydroxy-10-[bis(ethoxycarbonyl)methylene]anthrone, and 1-cyano-10-[bis (ethoxycarbonyl)methylene)anthrone, 7-nitro-2-aza-9-fluroenylidene-malononitrile, diphenoquinone derivatives, benzoquinone derivatives, naphthoquinone derivatives, quinine derivatives, tetracyanoethylenecyanoethylene, 2,4,8-trinitrothioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyanoquinoedimethane, 2,4,5,7-tetranitro-9-fluorenone, 5 2,4,7-trinitro-9-dicyanomethyleneneflurorenone, 2,4,5,7-tetranitroxanthone derivatives, and 2,4,8-trinitrothioxanthone derivatives.

If a particular charge transport material of this invention works as an electron transport compound, optionally, the organophotoreceptor of this invention may contain a charge transport compound. Suitable charge transport compounds include, but are not limited to, pyrazoline derivatives, fluorene derivatives, oxadiazole derivatives, stilbene derivatives, hydrazone derivatives, carbazole hydrazone derivatives, triaryl amines, polyvinyl carbazole, polyvinyl pyrene, polyacenaphthylene, or multi-hydrazone compounds comprising at least two hydrazone groups and at least two groups selected from the group consisting of triphenylamine and heterocycles such as carbazole, julolidine, phenothiazine, phenazine, phenoxazine, phenoxathiin, thiazole, oxazole, isoxazole, dibenzo(1,4)dioxine, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline. Preferably, the charge transport compound is an enamine stilbene compound such as MPCT-10, MPCT-38, and MPCT-46 from Mitsubishi Paper Mills (Tokyo, Japan).

For the multiple layer photoconductive elements, the charge generation layer comprises a binder in an amount of from about 10 to about 90 weight percent of the charge generation layer and preferably in an amount of from about 20 to about 75 weight percent of the charge generation layer, based on the weight of the charge generation layer. The charge transport layer typically comprises a charge transport compound in an amount of from about 25 to about 60 weight percent of the charge transport layer, based on the weight of the charge transport layer, and more preferably in an amount of from about 35 to about 50 weight percent, based on the weight of the charge transport layer, with the remainder of the charge transport layer comprising the binder, and optionally any conventional additives. The charge transport layer will typically have a thickness of from about 10 to about 40 microns and may be formed in accordance with any conventional technique known in the art.

For the single layer photoconductive elements, the charge generation compound is in an amount of from about 0.5 to about 20 weight percent and more preferably in an amount of from about 1 to about 10 weight percent, based on the weight of the photoconductive layer. The charge transport compound is in an amount of from about 10 to about 80 weight percent, based on the weight of the photoconductive layer, and more preferably in an amount of from about 40 to about 60 weight percent, based on the weight of the photoconductive layer. The electron transport compound is in an amount of from about 2.5 to about 25 weight percent, based on the weight of the photoconductive layer, and more preferably in an amount of from about 4 to about 20 weight percent, based on the weight of the photoconductive layer. The binder is in an amount of from about 15 to about 80 weight percent, based on the weight of the photoconductive layer, and more preferably in an amount of from about 20 to about 50 weight percent, based on the weight of the photoconductive layer.

Optionally, the organophotoreceptor of this invention, independently, may contain a light stabilizer. Non-limiting examples of suitable light stabilizer include hindered trialkylamines such as TINUVIN® 292 (from Ciba Specialty Chemicals, Terrytown, NY), hindered alkoxydialkylamines such as TINUVIN® 123 (from Ciba Specialty Chemicals), benzotriazoles such as TINUVIN® 928 (from Ciba Specialty Chemicals), benzophenones, nickel compounds such as ARBESTAB™ (from Robinson Brothers Ltd, West Midlands, Great Britain), salicylates, cyanocinnamates, benzylidene malonates, benzoates, oxanilides, polymeric sterically hindered amines such as LUCHEM™ (from Atochem North America, Buffalo, N.Y.). Preferably, the light stabilizer is selected from the group consisting of hindered trialkylamines having the following formula:

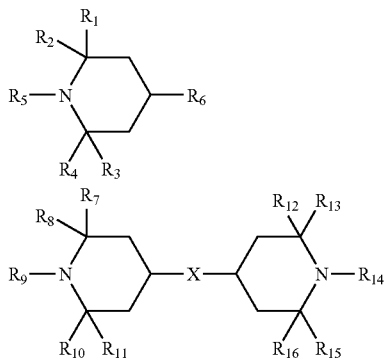

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, independently, hydrogen, alkyl group, or ester group, or ether group; and $R_5$, $R_9$, and $R_{14}$ are, independently, alkyl group; and X is a linking group selected from the group consisting of —O—CO—(CH$_2$)$_m$—CO—O— where m is between 2 to 20.

The light stabilizer in the photoconductive layer is in an amount of from about 0.5 to about 25 weight percent and more preferably in an amount of from about 1 to about 10 weight percent, based on the weight of the photoconductive layer.

Conveniently, the photoconductive layer may be formed by dispersing or dissolving the components such as a charge generating compound, a charge transport compound, a light stabilizer, an electron transport compound, and a polymeric binder in organic solvent, coating the dispersion and/or solution on the respective underlying layer and drying the coating. Preferably, the components are dispersed by high shear homogenization, ball-milling, attritor milling, high energy bead (sand) milling or other size reduction processes or mixing means known in the art for effecting particle size reduction in forming a dispersion.

The photoreceptor may include additional layers as well. Such layers are well-known and include, for example, barrier layers, release layers, adhesive layer, and sub-layer. The release layer forms the uppermost layer of the photoconductor element with the barrier layer sandwiched between the release layer and the photoconductive element. The adhesive layer locates and improves the adhesion between the barrier layer and the release layer. The sub-layer is a charge blocking layer and locates between the electrically conductive substrate and the photoconductive element. The sub-layer may also improve the adhesion between the electrically conductive substrate and the photoconductive element.

Suitable barrier layers include coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyninyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above organic binders optionally may contain small inorganic particles such as fumed silica, silica, titania, alumina, zirconia, or a combination thereof. The typical particle size is in the range of 0.001 to 0.5 micrometers, preferably 0.005 micrometers. A preferred barrier layer is a 1:1 mixture of methyl cellulose and methyl vinyl ether/maleic anhydride copolymer with glyoxal as a crosslinker.

The release layer topcoat may comprise any release layer composition known in the art. Preferably, the release layer is a fluorinated polymer, siloxane polymer, fluorosilicone polymer, silane, polyethylene, polypropylene, polyacrylate, or a combination thereof. More preferably, the release layers are crosslinked silicone polymers.

Typical adhesive layers include film forming polymers such as polyester, polyvinylbutyral, polyvinylpyrrolidone, polyurethane, polymethyl methacrylate, poly(hydroxy amino ether) and the like. Preferably, the adhesive layer is poly(hydroxy amino ether). If such layers are utilized, they preferably have a dry thickness between about 0.01 micrometer and about 5 micrometers.

Typical sub-layers include polyvinylbutyral, organosilanes, hydrolyzable silanes, epoxy resins, polyesters, polyamides, polyurethanes, silicones and the like. Preferably, the sub-layer has a dry thickness between about 20 Angstroms and about 2,000 Angstroms.

The charge transport compounds, and photoreceptors including these compounds, are suitable for use in an imaging process with either dry or liquid toner development. Liquid toner development is generally preferred because it offers the advantages of providing higher resolution images and requiring lower energy for image fixing compared to dry toners. Examples of useful liquid toners are well-known. They typically include a colorant, a resin binder, a charge director, and a carrier liquid. A preferred resin to pigment ratio is 2:1 to 10:1, more preferably 4:1 to 8:1. Typically, the colorant, resin, and the charge director form the toner particles.

The invention will now be described further by way of the following examples.

EXAMPLES

A. Synthesis

N-Phenyl-N-sulfolan-3-ylhydrazine

N-Phenyl-N-sulfolan-3-ylhydrazine can be prepared according to the procedure described in Great Britain Patent No. 1,047,525 by Mason, which is incorporated herein by reference. To a mixture of 0.5 mole of butadiene sulfone (commercially available from Aldrich, Milwaukee, Wis.) and 0.55 mole of phenylhydrazine (commercially available from Aldrich, Milwaukee, Wis.) was added 0.005 mole 40% aqueous potassium hydroxide solution. The mixture was kept for 2 hours at 60° C. whereupon a solid separated. After 10 hours the solid was filtered off to give N-phenyl-N-sulfolan-3-ylhydrazine (I) (93%) having a melting point of 119–20° C. (MeOH).

1,10-Bis(3-formyl-9-carbazolyl)decane

Carbazole (120 g, 0.72 mol, commercially obtained from Aldrich, Milwaukee, Wis.), dibromodecane (100 g, 0.33 mol, commercially obtained from Aldrich, Milwaukee, Wis.), and benzyltriethyl ammonium chloride (12 g) were dissolved in tetrahydrofuran (400 mL) and a concentrated solution of sodium hydroxide (120 g) in water (120 mL) was added. The mixture was heated at reflux with strong mechanical stirring for 4 hours, then cooled to room temperature and poured into an excess of water. The solid that precipitated was filtered off and the tetrahydrofuran layer was dried by magnesium sulfate and concentrated to dryness. The combined organic solids were recrystallized from tetrahydrofuran/water and dried in a vacuum oven to yield 116.5 g (69%, m.p.=130° C.) of 1,10-bis(9-carbazoyl)decane as an off-white solid.

Dimethylformamide (200 mL) was stirred and cooled in an ice bath while phosphorus oxychloride (70 mL, 115 g, 0.75 mol, commercially obtained from Aldrich, Milwaukee, Wis.) was gradually added. 1,10-bis(9-carbazolyl)decane (100 g, 0.22 mol) was introduced and the resulting mixture was heated on a steam bath with stirring for 1.5 hours. A viscous, dark brown liquid was generated from which a yellow solid precipitated upon cooling. This entire mixture was added to water (400 mL) and the crude product was filtered off at the pump, washed with water (200 mL), and then with a little ethanol. Recrystallization from tetrahydrofuran/water afforded 1,10-bis(3-formyl-9-carbazolyl)decane as light brown crystals (92.3 g, 83%, m.p.=122° C.).

1,8-Bis(3-formylcarbazolyl)octane

1,8-Bis(3-formylcarbazolyl)octane (m.p.=162° C.) was synthesized via an analogous procedure to that employed in the preparation of 1,10-bis(3-formyl-9-carbazolyl)decane, as described in the synthesis of Compound (2). Formylation was achieved in a 76% yield.

N-Pyrrol-2-yl-N-phenylhydrazine

N-Pyrrol-2-yl-N-phenylhydrazine can be prepared according to the procedure described in Japanese Patent No. 05148210 by Myamoto, which is incorporated herein by reference.

1-Phenyl-1-(1-benzyl-1H-tetrazol-5-yl)hydrazine

1-Phenyl-1-(1-benzyl-1H-tetrazol-5-yl)hydrazine can be prepared according to the procedure described in Tetrahedron (1983), 39(15), 2599–608 by Atherton et al., which is incorporated herein by reference.

N-(5-Benzotriazolyl)-N-phenylhydrazine

N-(5-benzotriazolyl)-N-phenylhydrazine can be prepared according to the procedure described below. To a mixture of phenylhydrazine (97 g, 0.9 mole, commercially available from Aldrich, Milwaukee, Wis.) and 5-chlorobenzotriazole (15.4 g, 0.1 mole, commercially available from Aldrich, Milwaukee, Wis.) heated to boiling temperature, sodium is slowly added until there is no more discharge of red coloration. After boiling for some time, the mixture is cooled to room temperature. The product is isolated and purified.

An N-phenylhydrazine Derivatives

An N-phenylhydrazine derivative can be prepared according to the procedure similar to that described in Zh. Org. Khim. (1967), 3(9), 1605-3 by Matevosyan et el., which is incorporated herein by reference. To a mixture of phenylhydrazine (97 g, 0.9 mole, commercially available from Aldrich, Milwaukee, Wis.) and p-9-(4-chlorobenzylidene) fluorene (28.9 g, 0.1 mole, commercially available from Aldrich, Milwaukee, Wis.) heated to boiling temperature, sodium was slowly added until there was no more discharge of red coloration. After boiling for some time, the mixture was dissolved in 1750 ml of ethanol and cooled to −15° C. The precipitated product was recrystallized to give a hydrazine having the formula $H_2N-NR_1R_2$, wherein $R_1$ is phenyl and wherein $R_2$ is the group A, wherein A is represented by the formula

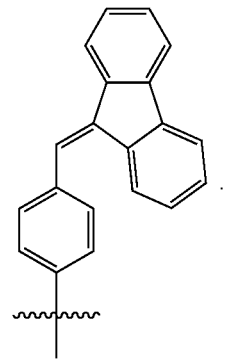

N-(4-Stilbenyl)-N-phenylhydrazine

N-(4-Stilbenyl)-N-phenylhydrazine can be prepared according to the procedure described in Zh. Org. Khim. (1967), 3(9), 1605-3 by Matevosyan et el., which is incorporated herein by reference. To a mixture of phenylhydrazine (97 g, 0.9 mole, commercially available from Aldrich, Milwaukee, Wis.) and p-chlorostilbene (21.4 g, 0.1 mole, commercially available from Spectrum Quality Products, Inc., Gardena, Calif.; Web: www.spectrumchemical.com) heated to boiling temperature, sodium was slowly added until there was no more discharge of red coloration. After boiling for some time, the mixture was dissolved in 1750 ml of ethanol and cooled to −15° C. The precipitated product was recrystallized to give 28% of N-(4-stilbenyl)-N-phenylhydrazine.

5-Methyl-1-Phenyl-3-(1-Phenylhydrazino)-Pyrazole

5-Methyl-1-phenyl-3-(1-phenylhydrazino)-pyrazole can be prepared according to the procedure described in J. Chem. Soc. C (1971), (12), 2314–17 by Boyd et el., which is incorporated herein by reference.

Compound (2)

To a 500 ml 3-neck RBF equipped with mechanical stirrer and reflux condenser were added 7 g of 1,10-Bis(3-formyl-9-carbazolyl)decane (0.013 mole, prepared as described in experimental section), 6 g of N-phenyl-N-sulfolan-3-ylhydrazine (0.026 mole, prepared as described in experimental section), 300 ml THF, and the mixture was refluxed for 5 hours. Cooled to RT and the volume was reduced to ~50 ml by evaporation and the solution was allowed to stand at RT for 1 hour where the solid came out which was filtered off and recrystalyzed 3 times from Toluene with activated charcoal. Obtained 10 g (80% yield). H-NMR in CDCl3:- τ=1.64–2.00(m,12H), 1.80–1.93(m,4H), 2.39–2.63(m,2H), 2.62–2.90(m,2H), 2.98–3.28(m,2H), 3.28–3.59(t,4H), 3.58–3.82(m,2H), 4.04–4.62(m,4H), 4.70–4.85(m,2H), 7.09–7.54(m,18H), 7.56–7.67(s,2H), 7.70–7.85(dd, 2H), 7.99–8.23(m,4H).

Compound (3)

Compound (3) can be prepared by the following procedure. 1,8-Bis(3-formyl-9-carbazolyl)octane (32 g, 64 mmol) and N-phenyl-N-sulfolan-3-ylhydrazine (29.38 g, 130 mmol, 2 equiv.) are combined in tetrahydrofuran (600 mL) and refluxed with stirring for 2 hours. Compound (3) is isolated and purified.

Compound (4)

Compound (4) can be prepared by the following procedure. 1,10-Bis(3-formyl-9-carbazolyl)decane (34 g, 64 mmol) and N-pyrrol-2-yl-N-phenylhydrazine (22.49 g, 130 mmol, 2 equiv.) are combined in tetrahydrofuran (600 mL) and heated at reflux with stirring for 2 hours. Compound (4) is isolated and purified.

Compound (5)

Compound (5) can be prepared by the following procedure. 1,8-Bis(3-formyl-9-carbazolyl)octane (32 g, 64 mmol) and N-pyrrol-2-yl-N-phenylhydrazine (22.49 g, 130 mmol, 2 equiv.) are combined in tetrahydrofuran (600 mL) and refluxed with stirring for 2 hours. Compound (5) is isolated and purified.

Compound (6)

Compound (6) can be prepared by the following procedure. 1,10-Bis(3-formyl-9-carbazolyl)decane (34 g, 64 mmol) and 1-Phenyl-1-(1-benzyl-1H-tetrazol-5-yl)hydrazine (34.58 g, 130 mmol, 2 equiv.) are combined in tetrahydrofuran (600 mL) and heated at reflux with stirring for 2 hours. Compound (6) is isolated and purified.

Compound (7)

Compound (7) can be prepared by the following procedure. 1.8-Bis(3-formyl-9-carbazolyl)octane (32 g, 64 mmol) and 1-Phenyl-1-(1-benzyl-1H-tetrazol-5-yl)hydrazine (34.58 g, 130 mmol, 2 equiv.) are combined in tetrahydrofuran (600 mL) and heated at reflux with stirring for 2 hours. Compound (7) is isolated and purified.

Compound (8)

Compound (8) can be prepared by the following procedure. 1,10-Bis(3-formyl-9-carbazolyl)decane (34 g, 64 mmol) and N-(5-benzotriazolyl)-N-phenylhydrazine (29.25 g, 130 mmol, 2 equiv.) are combined in tetrahydrofuran (600 mL) and heated at reflux with stirring for 2 hours. Compound (8) is isolated and purified.

Compound (9)

Compound (9) can be prepared by the following procedure. 1.8-Bis(3-formyl-9-carbazolyl)octane (32 g, 64 mmol) and N-(5-benzotriazolyl)-N-phenylhydrazine (29.25 g, 130 mmol, 2 equiv.) are combined in tetrahydrofuran (600 mL) and heated at reflux with stirring for 2 hours. Compound (9) is isolated and purified.

Compound (10)

Compound (10) can be prepared by the following procedure. 1,10-Bis(3-formyl-9-carbazolyl)decane (34 g, 64 mmol) and a hydrazine having the formula $H_2N—NR_1R_2$, wherein $R_1$ is phenyl and wherein $R_2$, is the runup A wherein A is represented by the formula

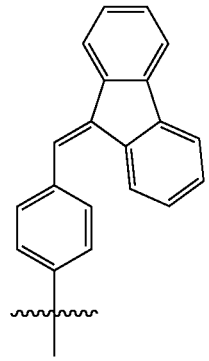

(46.8 g, 130 mmol, 2 equiv.) are combined in tetrahydrofuran (600 mL) and heated at reflux with stirring for 2 hours. Compound (10) is isolated and purified.

Compound (11)

Compound (11) can be prepared by the following procedure. 1.8-Bis(3-fomyl-9-carbazoly)octane (32 g, 64 mmol) and a hydrazine having the formula $H_2N—NR_1R_2$, wherein $R_1$, is phenyl and wherein $R_2$, is the group A, wherein A is represented by the formula

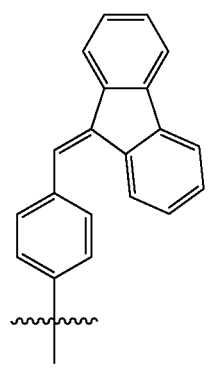

(46.8 g. 130 mmol, 2 equiv.) are combined in tefrahydrofuran (600 mL) and heated at refiux with stirring for 2 hours. Compound (11) is isolated and purified.

Compound (12)

Compound (12) can be prepared by the following procedure. 1,10-Bis(3-formyl-9-carbazolyl)decane (34 g, 64 mmol) and N-(4-stilbenyl)-N-phenylhydrazine (37.18 g, 130 mmol, 2 equiv.) are combined in tetrahydrofuran (600 mL) and heated at reflux with stirring for 2 hours. Compound (12) is isolated and purified.

Compound (13)

Compound (13) can be prepared by the following procedure. 1,8-Bis(3-formyl-9-carbazolyl)octane (32 g, 64 mmol) and N-(4-stilbenyl)-N-phenylhydrazine (37.18 g, 130 mmol, 2 equiv.) are combined in tetrahydrofuran (600 mL) and heated at reflux with stirring for 2 hours. Compound (13) is isolated and purified.

Compound (14)

To a 100 ml RBF equipped with reflux condenser and mechanical stirrer were added 7.92 g of 1,10-Bis(3-formyl-9-carbazolyl)decane (0.015 mole, prepared as in experimental section), 2.5 g of 4-methylsulfonylphenylhydrazine (0.03 mole, commercially available from Fisher Scientific USA, Pittsburgh, Pa.), 100 of Toluene and few drops of concentrated sulfuric acid and the mixture was refluxed for 6 hours. The product was recrystalyzed 3 times from ethylacetate and charcoal. Obtained 3.9 g (40% yield). H-NMR in CDCl3:- τ=0.97–1.33(m,12H), 1.58–1.83(m,4H), 3.07–3.17(s,6H), 4.20–4.53(t,4H), 7.10–7.75(m,16H), 7.85–7.90(s,2H), 8.10–8.23(dd, 2H), 8.27–8.50(m,4H)

Compound (15)

Compound (15) can be prepared by the following procedure. 1,8-Bis(3-formyl-9-carbazolyl)octane (32 g, 64 mmol) and 4-methylsulfonylphenylhydrazine (24.18 g, 130 mmol, 2 equiv., commercially available from Fisher Scientific USA, Pittsburgh, Pa.) are combined in tetrahydrofuran (600 mL) and heated at reflux with stirring for 16 hours. Compound (15) is isolated and purified.

Compound (16)

Compound (16) can be prepared by the following procedure. 1,10-Bis(3-formyl-9-carbazolyl)decane (34 g, 64 mmol) and 4-(methylsulfonyl)-2-nitrophenylhydrazine (30.03 g, 130 mmol, 2 equiv., commercially available from Aldrich, Milwaukee, Wis.) are combined in tetrahydrofuran (600 mL) and heated at reflux with stirring for 16 hours. Compound (16) is isolated and purified.

Compound (17)

Compound (17) can be prepared by the following procedure. 1,10-Bis(3-formyl-9-carbazolyl)decane (34 g, 64 mmol) and 5-methyl-1-phenyl-3-(1-phenylhydrazino)pyrazole (34.32 g, 130 mmol, 2 equiv.) are combined in tetrahydrofuran (600 mL) and heated at reflux with stirring for 2 hours. Compound (17) is isolated and purified.

Compound (18)

Compound (18) can be prepared by the following procedure. 1,8-Bis(3-formyl-9-carbazolyl)octane (32 g, 64 mmol) and 5-methyl-1-phenyl-3-(1-phenylhydrazino)pyrazole (34.32 g, 130 mmol, 2 equiv.) are combined in tetrahydrofuran (600 mL) and heated at reflux with stirring for 2 hours. Compound (18) is isolated and purified.

B. Dual Layer Organophotoreceptor Preparation Methods

An inverted dual layer organophotoreceptor can be prepared by incorporating Compounds (2)–(18). A charge transport solution containing 50 wt. % of one the compounds in Polycarbonate Z binder can be prepared by combining a solution of 1.25 g of the compound in 8.0 g of tetrahydrofuran with 1.25 g of Polycarbonate Z in 2.50 g of toluene. The charge transport solution is then hand knife-coated onto a 3 mil (76 micrometer) thick aluminized polyethylene terephthalate film (MELINEX™ 442 polyester film from Dupont having a 1 ohm/square aluminum vapor coat) having a 0.3 micron polyester resin sub-layer (VITEL™ PE-2200 from Bostik, Middletown, Mass.) and dried to form a charge transport layer having a thickness of 9 micrometers.

A dispersion can be prepared by micronising 700 g of suspension consisting of 112.7 g of oxytitanium phthalocyanine pigment (H.W. Sands Corp., Jupiter, Fl), 49 g of S-LEC B™ Bx-5 polyvinylbutryal resin (Sekisui Chemical Co. Ltd.), and 651 g of methyl ethyl ketone using a horizontal sand mill operating in recirculation mode for 8 hours. A 10 g portion of the resulting dispersion is diluted by 3-fold with methyl ethyl ketone then hand knife-coated onto the charge transport layer from the preceding paragraph and dried at 80° C. for 10 minutes to form a charge generating layer having a thickness of 0.27 micrometer.

C. Single Layer Organophotoreceptor Preparation Methods

Single layer organophotoreceptor can be prepared by incorporating Compounds (2)–(18). A single layer organophotoreceptor is fabricated by hand knife-coating a solution onto a 76.2 micron (3 mil) thick polyester substrate with a layer of vapor-coated aluminum (commercially obtained from CP Films, Martinsville, Va.). The coating solution for the single layer organophotoreceptor was prepared by combining 2.4 g of a premix solution containing 20 wt % electron transport compound in tetrahydrofuran, 6.66 g of a premix solution containing 25 wt % charge transfer material in tetrahydrofuran, 7.67 g of of a premix solution containing 12% polyvinyl butyral resin (BX-1, commercially obtained from Sekisui Chemical Co. Ltd., Japan) in tetrahydrofuran, 0.74 g of the CGM mill-base containing 19% of titanyl oxyphthalocyanine and a polyvinyl butyral resin (BX-5, commercially obtained from Sekisui Chemical Co. Ltd., Japan) at a ratio of 2.3:1, and an additional 0.34 g of tetrahydrofuran to produce a final solution containing 18 wt % solids. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 1-micron zirconium beads using recycle mode for 4–8 hours. After mixing the final solution on a mechanical shaker for ~1 hour, the single layer coating solution was coated onto the substrate described above using a knife coater with a gap space of 94 micron followed by drying in an oven at 110° C. for 5 minutes.

Comparative Example A

Comparative Example A was a single layer organophotoreceptor having a 76.2 micron (3 mil) thick polyester substrate having a layer of vapor-coated aluminum (commercially obtained from CP Films, Martinsville, Va.). The coating solution for the single layer organophotoreceptor was prepared by pre-mixing 2.4 g of 20% (4-n-butoxycarbonyl-9-fluorenylidene) malononitrile in tetrahydrofuran, 6.66 g of 25% MPCT-10 (a charge transfer material, commercially obtained from Mitsubishi Paper Mills, Tokyo, Japan) in tetrahydrofuran, 7.65 g of 12% polyvinyl butyral resin (BX-1, commercially obtained from Sekisui Chemical Co. Ltd., Japan) in tetrahydrofuran. To the above mixture was then added 0.74 g of a CGM mill-base containing 19% of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 1-micron zirconium beads using recycle mode for 4 hours. After mixing on a mechanical shaker for ~1 hour, the single layer coating solution was coated onto the substrate described above using a knife coater with a gap space of 94 micron followed by drying in an oven at 110° C. for 5 minutes.

Example 1

This Example was a single layer organophotoreceptor having a 76.2 micron (3 mil) thick polyester substrate having a layer of vapor-coated aluminum (commercially obtained from CP Films, Martinsville, Va.). The coating solution for the single layer organophotoreceptor was prepared by pre-mixing 2.4 g of 20% Compound 14 in tetrahydrofuran, 6.66 g of 25% MPCT-10 (a charge transfer material, commercially obtained from Mitsubishi Paper Mills, Tokyo, Japan) in tetrahydrofuran, 7.65 g of 12% polyvinyl butyral resin (BX-1, commercially obtained from Sekisui Chemical Co. Ltd., Japan) in tetrahydrofuran. To the above mixture was then added 0.74 g of a CGM mill-base containing 19% of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 1-micron zirconium beads using recycle mode for 4 hours. After mixing on a mechanical shaker for ~1 hour, the single layer coating solution was coated onto the substrate described above using a knife coater with a gap space of 94 micron followed by drying in an oven at 110° C. for 5 minutes.

D. Electrostatic Testing

Extended electrostatic cycling performance of the charge transfer compounds of this invention is determined using an in-house designed and developed test bed that tests up to 3 samples strips that are wrapped around a drum. The three coated sample strips, each measuring 50 cm long by 8.8 cm wide, were fastened side-by-side and completely around an aluminum drum (50.3 cm circumference). At least one of the strips was a control sample (e.g., Compound 2 in U.S. Pat. No. 6,140,004) that was precision web coated and used as an internal reference point. In this electrostatic cycling tester, the drum rotated at a rate of 8.13 cm/s (3.2 ips) and the location of each station in the tester (distance and elapsed time per cycle) is given as:

Electrostatic test stations around the sample sheet wrapped drum.

| Station | Degrees | Total Distance, cm | Total Time, sec |
|---|---|---|---|
| Front erase bar edge | 0° | Initial, 0 cm | Initial, 0 s |
| Erase Bar | 0–7.2° | 0–1.0 | 0–0.12 |
| Scorotron | 113.1–135.3° | 15.8–18.9 | 1.94–2.33 |
| Laser Strike | 161.0° | 22.5 | 2.77 |
| Probe #1 | 181.1° | 25.3 | 3.11 |
| Probe #2 | 251.2° | 35.1 | 4.32 |
| Erase bar | 360° | 50.3 | 6.19 |

From the table, the first electrostatic probe (TREK™ 344 electrostatic meter) is located 0.34 s after the laser strike station and 0.78 s after the scorotron. Also, the second probe (TREK™ 344 electrostatic meter) is located 1.21 s from the first probe and 1.99 s from the scorotron. All measurements were performed at ambient temperature and relative humidity.

Electrostatic measurements were obtained as a compilation of several tests. The first three diagnostic tests (prodstart, VlogE initial, dark decay initial) are designed to evaluate the electrostatic cycling of a new, fresh sample and the last three, identical diagnostic tests (prodend, VlogE final, dark decay final) are run after cycling of the sample (longrun).

1. PRODTEST: Charge acceptance ($V_{acc}$) and discharge voltage ($V_{dis}$) were established by subjecting the samples to corona charging (erase bar always on) for three complete drum revolutions (laser off); discharged with the laser @ 780 nm & 600 dpi on the forth revolution; completely charged for the next three revolutions (laser off); discharged with only the erase lamp @ 720 nm on the eighth revolution (corona and laser off) to obtain residual voltage ($V_{res}$); and, finally, completely charged for the last three revolutions (laser off). The contrast voltage ($V_{con}$) is the difference between $V_{acc}$ and $V_{dis}$.

2. VLOGE: This test measures the photoinduced discharge of the photoconductor to various laser intensity levels by monitoring the discharge voltage of the belt as a function of the laser power (exposure duration of 50 ns) with fixed exposure times and constant initial potentials.

3. DARK DECAY: This test measures the loss of charge acceptance with time without laser or erase illumination for 90 seconds and can be used as an indicator of i) the injection of residual holes from the charge generation layer to the charge transport layer, ii) the thermal liberation of trapped charges, and iii) the injection of charge from the surface or aluminum ground plane.

4. LONGRUN: The belt was electrostatically cycled for 100 drum revolutions according to the following sequence per each belt-drum revolution. The belt was charged by the corona, the laser was cycled on and off (80–100° sections) to discharge a portion of the belt and, finally, the erase lamp discharged the whole belt in preparation for the next cycle. The laser was cycled so that the first section of the belt was never exposed, the second section was always exposed, the third section was never exposed, and the final section was always exposed. This pattern was repeated for a total of 100 drum revolutions and the data for every $5^{th}$ cycle was recorded.

5. After the 100th cycle (long run test), the PRODTEST, VLOGE, DARK DECAY diagnostic tests were run again.

TABLE 1

Electrostatic Testing Results after 100 cylces.

| | Prodstart | | | | | | Prodstop | | | | |
|---|---|---|---|---|---|---|---|---|---|---|---|
| Sample | $V_{acc}$ | $V_{dis}$ | $V_{con}$ | Sensitivity | Dark Decay | $V_{res}$ | $V_{acc}$ | $V_{dis}$ | $V_{con}$ | Dark Decay | $V_{res}$ |
| Comparative Example A | 620 | 36 | 584 | 377 | 42 | 12 | 621 | 34 | 587 | 41 | 10 |
| Example 1 | 597 | 69 | 528 | 314 | 33 | 34 | 421 | 59 | 351 | 32 | 33 |

E. Ionization Potential Protocol

Samples for ionization potential (Ip) measurements were prepared by dissolving Compounds 2 and 14 independently in tetrahydrofuran. Each solution was hand-coated on an aluminized polyester substrate that was precision coated with a methylcellulose-based adhesion sub-layer to form a charge transport material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of both the sub-layer and CTM layer was ~0.4 µm. No binder material was used with CTM in the preparation of the samples for Ip measurements.

The ionization potential was measured by the electron photoemission in air method similar to that described in "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama, which is hereby incorporated by reference. The samples were illuminated with monochromatic light from the quartz monochromator with a deuterium lamp source. The power of the incident light beam was $2-5 \cdot 10^{-8}$ W. The negative voltage of $-300$ V was supplied to the sample substrate. The counter-electrode with the $4.5 \times 15$ mm² slit for illumination was placed at 8 mm distance from the sample surface. The counter-electrode was connected to the input of the BK2-16 type electrometer, working in the open impute regime, for the photocurrent measurement. A $10^{-15}-10^{-12}$ amp photocurrent was flowing in the circuit under illumination. The photocurrent, I, was strongly dependent on the incident light photon energy hv. The $I^{0.5}=f(h\nu)$ dependence was plotted. Usually the dependence of the square root of photocurrent on incident light quanta energy is well described by linear relationship near the threshold [see references "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama; and "Photoemission in Solids", Topics in Applied Physics, 26, 1–103 (1978) by M. Cordona and L. Ley]. The linear part of this dependence was extrapolated to the hv axis and Ip value was determined as the photon energy at the interception point. The ionization potential measurement has an error of ±0.03 eV. The ionization potential data are listed in Table 2.

F. Hole Mobility

Samples for charge carrier mobility measurements were prepared by dissolving Compounds 2 and 14 independently in tetrahydrofuran with a binder to form 10% solid solutions. The binder was polycarbonate Z 200 (commercially obtained from Mitsubishi Engineering Plastics, White Plains, N.Y.). The sample/binder ratio was 4:6 or 5:5. Each solution was coated on an aluminized polyester substrate to form a charge transport material (CTM) layer. The thickness of the CTM layer varied in the range of 5–10 µm.

The hole drift mobility was measured by a time of flight technique as described in "The discharge kinetics of negatively charged Se electrophotographic layers," Lithuanian Journal of Physics, 6, p. 569–576 (1966) by E. Montrimas, V. Gaidelis, and A. Pažėra, which is hereby incorporated by reference. Positive corona charging created electric field inside the CTM layer. The charge carriers were generated at the layer surface by illumination with pulses of nitrogen laser (pulse duration was 2 ns, wavelength 337 nm). The layer surface potential decreased as a result of pulse illumination was up to 1–5% of initial potential before illumination. The capacitance probe that was connected to the wide frequency band electrometer measured the speed of the surface potential dU/dt. The transit time $t_t$ was determined by the change (kink) in the curve of the dU/dt transient in linear or double logarithmic scale. The drift mobility was calculated by the formula $\mu = d^2/U_0 \cdot t_t$, where d is the layer thickness and $U_0$ is the surface potential at the moment of illumination.

Mobility values at electric field strength, E, of $6.4 \cdot 10^5$ V/cm are given in the Table 2. The mobility field dependencies may be approximated by the function $$\mu \sim e^{\alpha \sqrt{E}}$$

where α is parameter characterizing mobility field dependence. The value of the parameter α is also given in Table 2.

TABLE 2

| Compound | Hole Mobility (cm²/Vs) | A | $I_p$ (eV) |
|---|---|---|---|
| 2 | $\sim 2 \cdot 10^{-8}$ | 0.008 | 5.7 |
| 14 | $2 \cdot 10^{-8}$ | 0.006 | ~5.65 |

In the presentation of materials, proportions, elements, components, subcomponents, equipment and steps in processes, the examples provided are intended to be exemplary of the generic nature of the invention and are not intended to limit the scope of the invention. Alternatives of the specific examples within the generic scope of the invention described in the specification will be apparent to those skilled in the art. Those alternative concepts are enabled by the specific disclosure and specific examples and are not excluded by a narrower exemplification. These other embodiments are within the invention and within the following claims.

What is claimed is:

1. An electrophotographic imaging process comprising:
(a) applying an electrical charge to a surface of an organophotoreceptor comprising:
(i) a charge transport compound having the formula

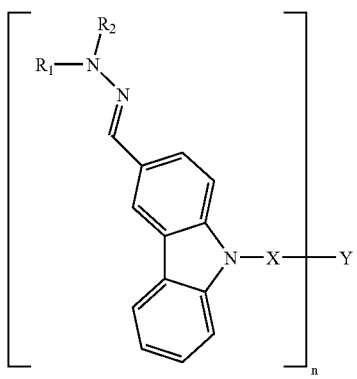

where n is an integer between 2 and 6, inclusive;
$R_2$ is a sulfolanyl group; a pyrrolyl group; a tetrazolyl group; a benzotriazolyl group; a stilbenyl group; an alkylsulfonylphenyl group, an arylsulfonylphenyl; a pyrazolyl group; or group A, wherein A is represented by the formula

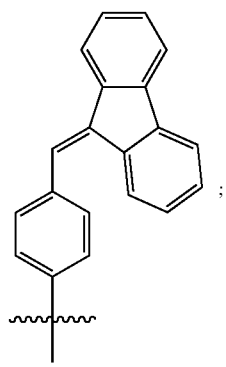

$R_1$ may be hydrogen, an alkyl group, or an aryl group with the proviso that when $R_2$ is a sulfolanyl group, a pyrrolyl group, a tetrazolyl group, a benzotriazolyl group, the group A, a stilbenyl group, or a pyrazolyl group, $R_1$ is an aryl group;
X is an alkylene linking group having the formula $-(CH_2)_m-$, where m is an integer between 0 and 20, inclusive, and one or more methylene groups in the alkylene group is optionally replaced by an oxygen atom, a carbonyl group, urethane, urea, an ester group, a $-NR_3$, group, a $CHR_4$ group, or a $CR_5R_6$ group where $R_3$, $R_4$, $R_5$, and $R_6$ are, independently, H, an alkyl group, or aryl group; and
Y is a bond, carbon atom, nitrogen atom, oxygen atom, sulfur atom, a $-(CH_2)_p-$ group where p is an integer between 0 and 10, an aryl group, a cycloalkyl group, a cyclosiloxyl group, a heterocyclic group, or a $CR_7$ group where $R_7$ is hydrogen atom, an alkyl group, or aryl group;
(ii) a charge generating compound; and
(iii) an electrically conductive substrate;

(b) imagewise exposing said surface of said organophotoreceptor to radiation to dissipate charge in selected areas and thereby form a pattern of charged and uncharged areas on said surface;
(c) contacting said surface with a liquid toner comprising a dispersion of colorant particles in an organic liquid to create a toned image; and
(d) transferring said toned image to a substrate.

2. The electrophotograpbie imaging process of claim 1 wherein said organophotoreceptor is in the form of a flexible belt or a drum.

3. The electrophotographic imaging process of claim 1 wherein said organophotoreceptor comprises:
(a) a charge transport layer comprising said charge transport compound and a polymeric binder;
(b) a charge generating layer comprising said charge generating compound and a polymeric binder; and
(c) said electrically conductive substrate.

4. The electrophotographic imaging process of claim 1 wherein said charge transport compound has the general formula

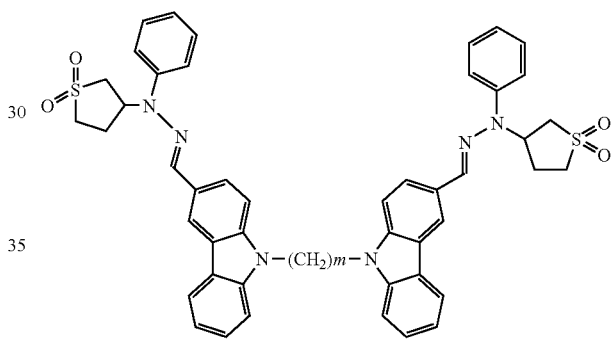

where m is an integer between 2 and 20.

5. The electrophotographic imaging process of claim 1 wherein $R_2$ is a sulfolanyl group, and X is a linking group having the formula $-(CH_2)_m-$, where m is an integer between 0 and 20, inclusive.

6. The electrophotographic imaging process of claim 1 wherein $R_2$ is a pyrrolyl group and X is a linking group having the formula $-(CH_2)_m-$, where m is an integer between 0 and 20, inclusive.

7. The electrophotographic imaging process of claim 1 wherein $R_2$ is a tetrazolyl group; and X is a linking group having the formula $-(CH_2)_m-$, where m is an integer between 0 and 20, inclusive.

8. The electrophotographie imaging process of claim 1 wherein $R_2$ is a benzotriazolyl group; and X is a linking group having the formula $-(CH_2)_m-$, where in is an integer between 0 and 20, inclusive.

9. The electrophotographic imaging process of claim 1 wherein $R_2$ is the group A; and X is a linking group having the formula $-(CH_2)_m-$, where m is an integer between 0 and 20, inclusive.

10. The electrophotographic imaging process of claim 1 wherein $R_2$ is a stilbenyl group; and X is a linking group having the formula $-(CH_2)_m-$, where m is an integer between 0 and 20, inclusive.

11. The electrophotographic imaging process of claim 1 wherein $R_2$ is a pyrazolyl group; and X is a linking group having the formula —$(CH_2)_m$—, where m is an integer between 0 and 20, inclusive.

12. The electrophotographic imaging process of claim 1 wherein $R_2$ is an alkylsulfonylphenyl group or an arylsulfonylphenyl $R_1$ may be hydrogen, an alkyl group, or an sql group; and X is a linking group having the formula —$(CH_2)_m$—, where m is an integer between 0 and 20, inclusive.

13. The electrophotograpbie imaging process of claim 1 wherein said charge transport compound is selected from the group consisting of the following formulae:

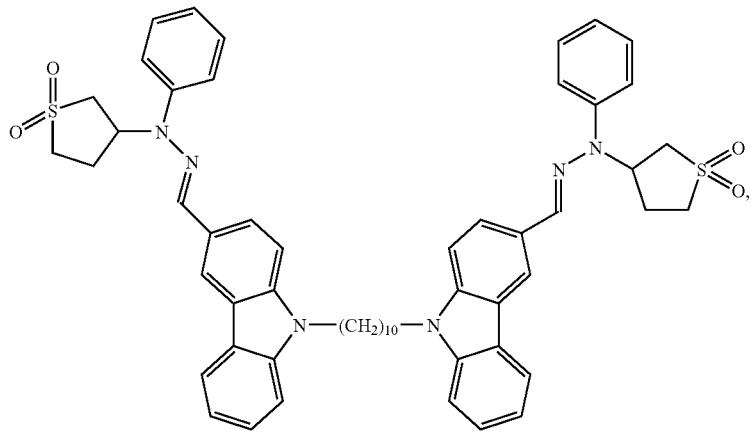

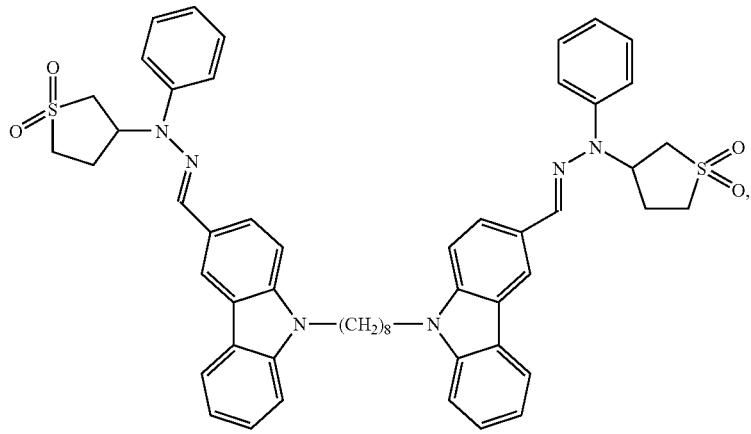

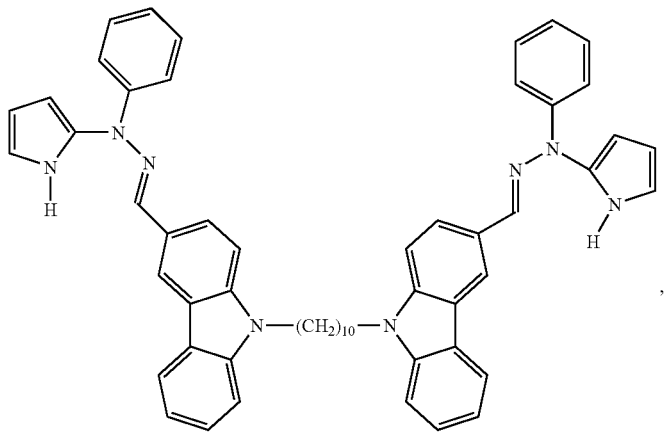

-continued
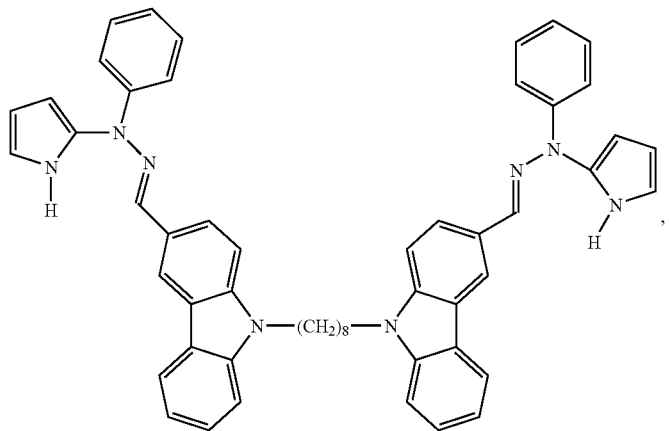
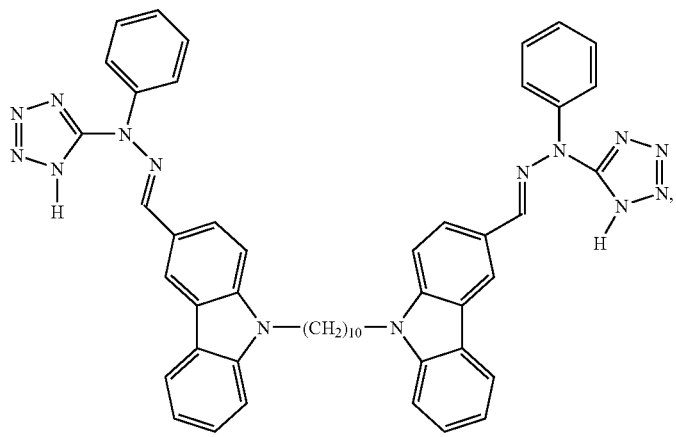
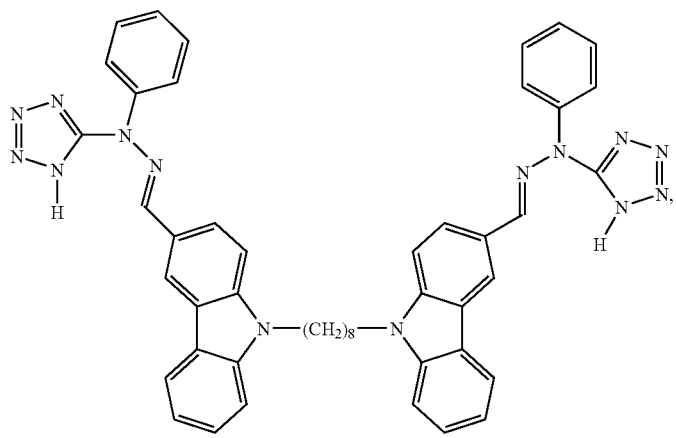

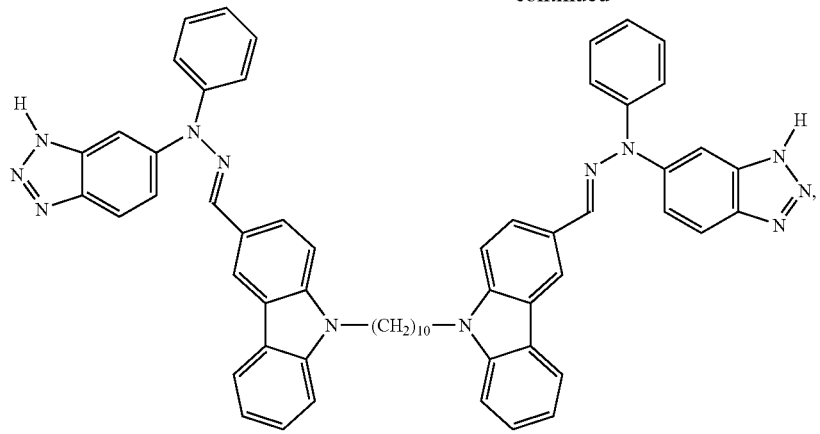
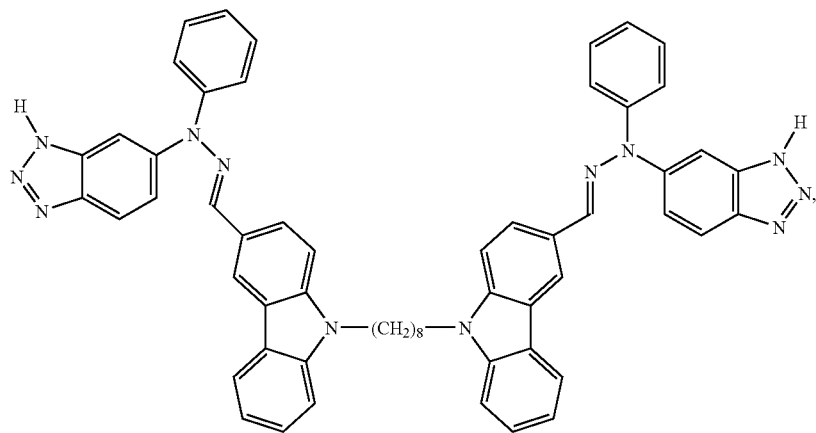
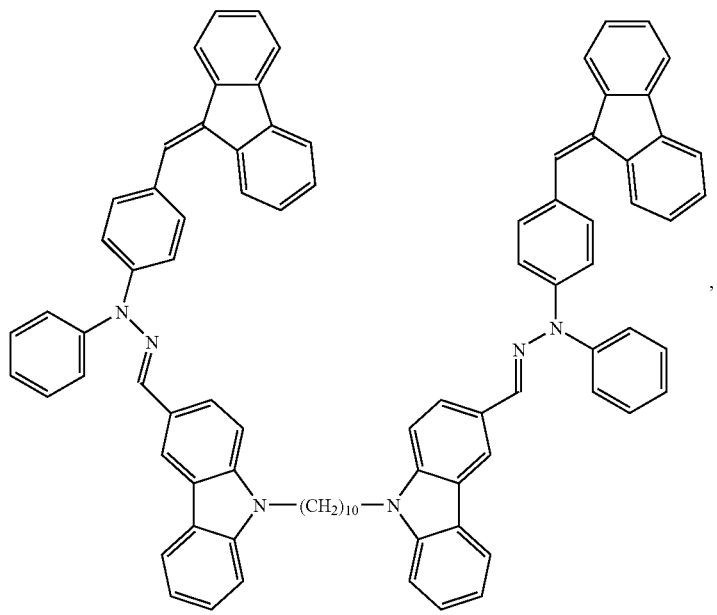

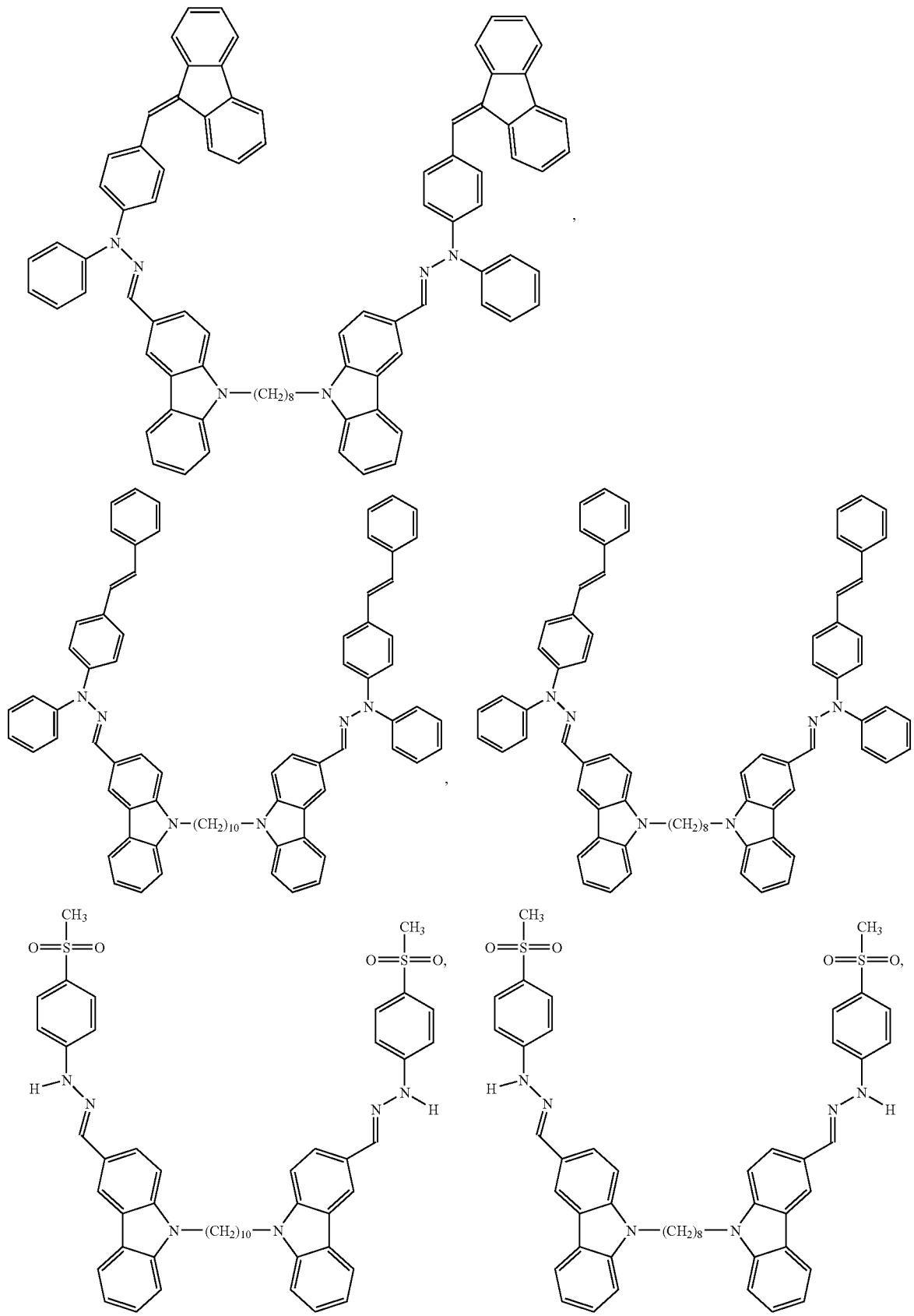

-continued
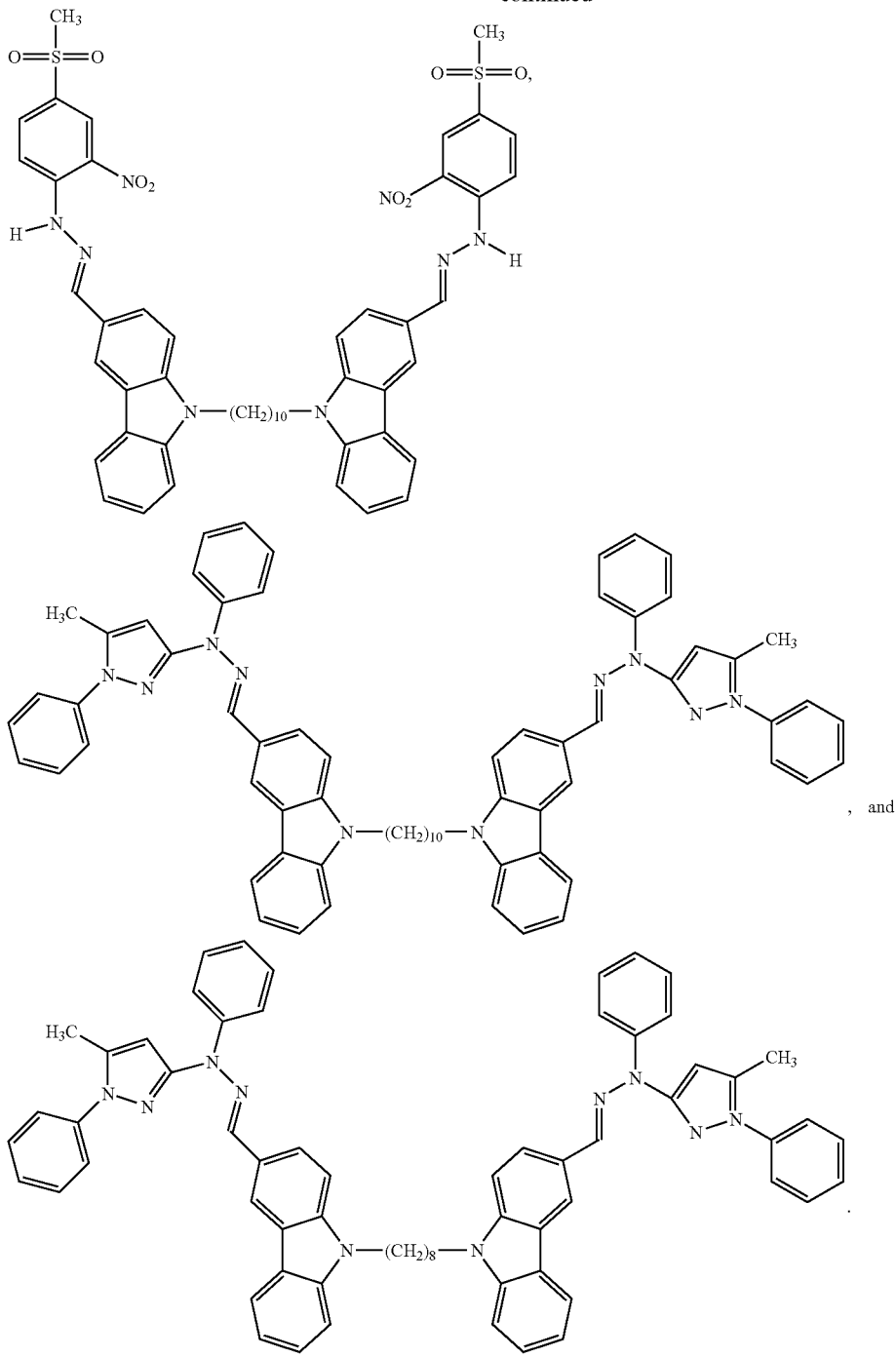
, and
* * * * *